US011292789B1

United States Patent
Na et al.

(12)

(10) Patent No.: US 11,292,789 B1
(45) Date of Patent: Apr. 5, 2022

(54) COMPOSITION FOR INHIBITING GROWTH OF SARS-COV-2 AND METHOD OF PREPARING THE SAME

(71) Applicants: Medicare Pharmaceuticals Inc., Jeollabuk-do (KR); MEDICARE LC., Jeollabuk-do (KR)

(72) Inventors: Do Hyun Na, Seoul (KR); Kyung Pyo Kang, Seoul (KR); Jin Hwan Jun, Seoul (KR); Geon Go, Seoul (KR); Hyeon Jun Na, Seoul (KR); Sang Jin Kang, Seoul (KR); Young Hyun Na, Seoul (KR); Se Jin Yoon, Seoul (KR); Su Ji Na, Seoul (KR)

(73) Assignees: Medicare Pharmaceuticals Inc., Wanju-gun (KR); MEDICARE LC., Wanju-gun (KR)

( * ) Notice: Subject to any disclaimer, the term of this patent is extended or adjusted under 35 U.S.C. 154(b) by 0 days.

(21) Appl. No.: 17/106,799

(22) Filed: Nov. 30, 2020

(30) Foreign Application Priority Data

Oct. 16, 2020 (KR) .......................... 10-2020-0134352

(51) Int. Cl.
| | | |
|---|---|---|
| *A61P 31/14* | (2006.01) | |
| *A61K 31/517* | (2006.01) | |
| *C07D 239/91* | (2006.01) | |
| *C07D 455/02* | (2006.01) | |
| *A61K 35/66* | (2015.01) | |

(52) U.S. Cl.
CPC .......... *C07D 455/02* (2013.01); *A61K 31/517* (2013.01); *A61K 35/66* (2013.01); *A61P 31/14* (2018.01); *C07D 239/91* (2013.01)

(58) Field of Classification Search
CPC ........................... C07D 239/91; A61K 31/517
See application file for complete search history.

(56) References Cited

FOREIGN PATENT DOCUMENTS

KR  10-0664724 B1  1/2007

OTHER PUBLICATIONS

Taeyoon Kim, "Medicare Group succeeds in developing new drug to inhibit COVID-19 strains", Money Today, Jul. 2020.
In-Kyoung Lee et al., "Dictyoquinazols A, B, and C, New Neuroprotective Compounds from the Mushroom Dictyophora indusiata", Journal of Natural Products, Dec. 2002, vol. 65, No. 12, pp. 1769-1772.
Yuvixza Lizarme et al., "Synthesis and neuroprotective activity of dictyoquinazol A and analogues", Bioorganic & Medicinal Chemistry, Feb. 2016, vol. 24, No. 7, pp. 1480-1487.
Spencer J. Williams et al., "[alpha]-glucosidase inhibitors as host-directed antiviral agents with potential for the treatment of COVID-19", Biochemical Society Transactions, Jun. 2020, vol. 48, No. 3, pp. 1287-1295.
Communication dated Apr. 30, 2021, issued by the European Patent Office in counterpart European Application No. 20210702.5.
Solomon Habtemariam, "The Chemistry, Pharmacology and Therapeutic Potential of the Edible Mushroom Dictyophora indusiata (Vent ex. Pers.) Fischer (Synn. *Phallus indusiatus*)", Biomedicines, Dec. 12, 2019, pp. 1-21, 7, 98.

*Primary Examiner* — Susanna Moore
(74) *Attorney, Agent, or Firm* — Sughrue Mion, PLLC

(57) ABSTRACT

Disclosed is a composition for inhibiting the growth of virus. More particularly, the composition for inhibiting the growth of virus includes MDPX-V2021 represented by Formula 1, wherein MDPX-V2021 serves to inhibit a post-translational modification (PTM) stage in cells after SARS-CoV-2 penetrates into the body.

10 Claims, 5 Drawing Sheets

[FIG. 1]
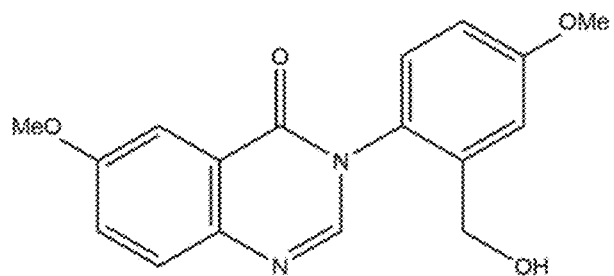
[FIG. 2]
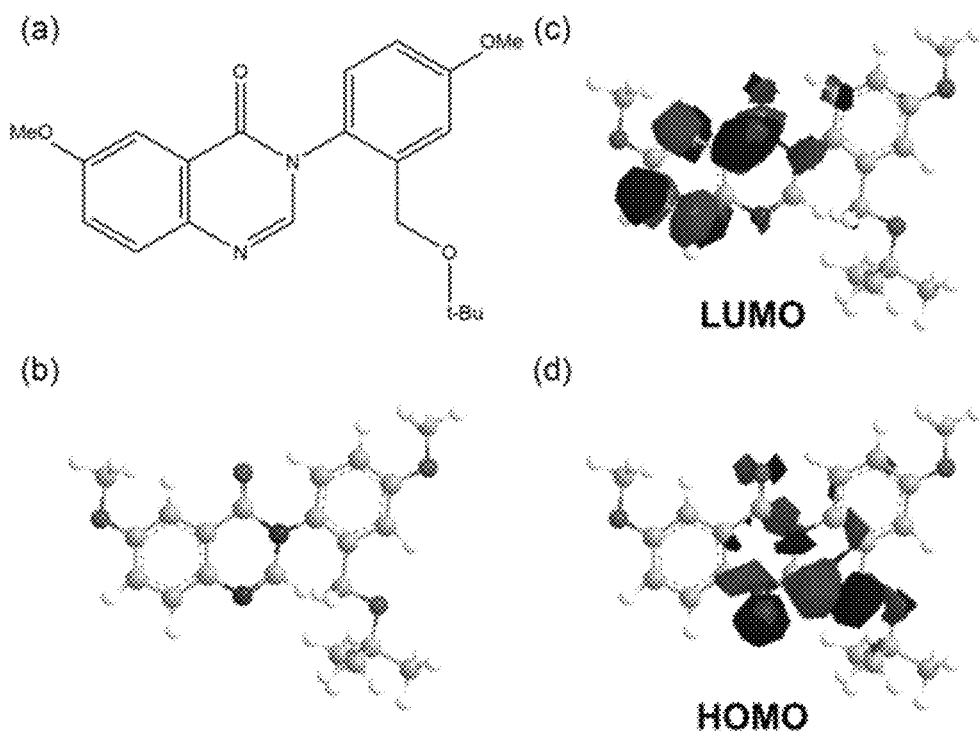

[FIG. 3]
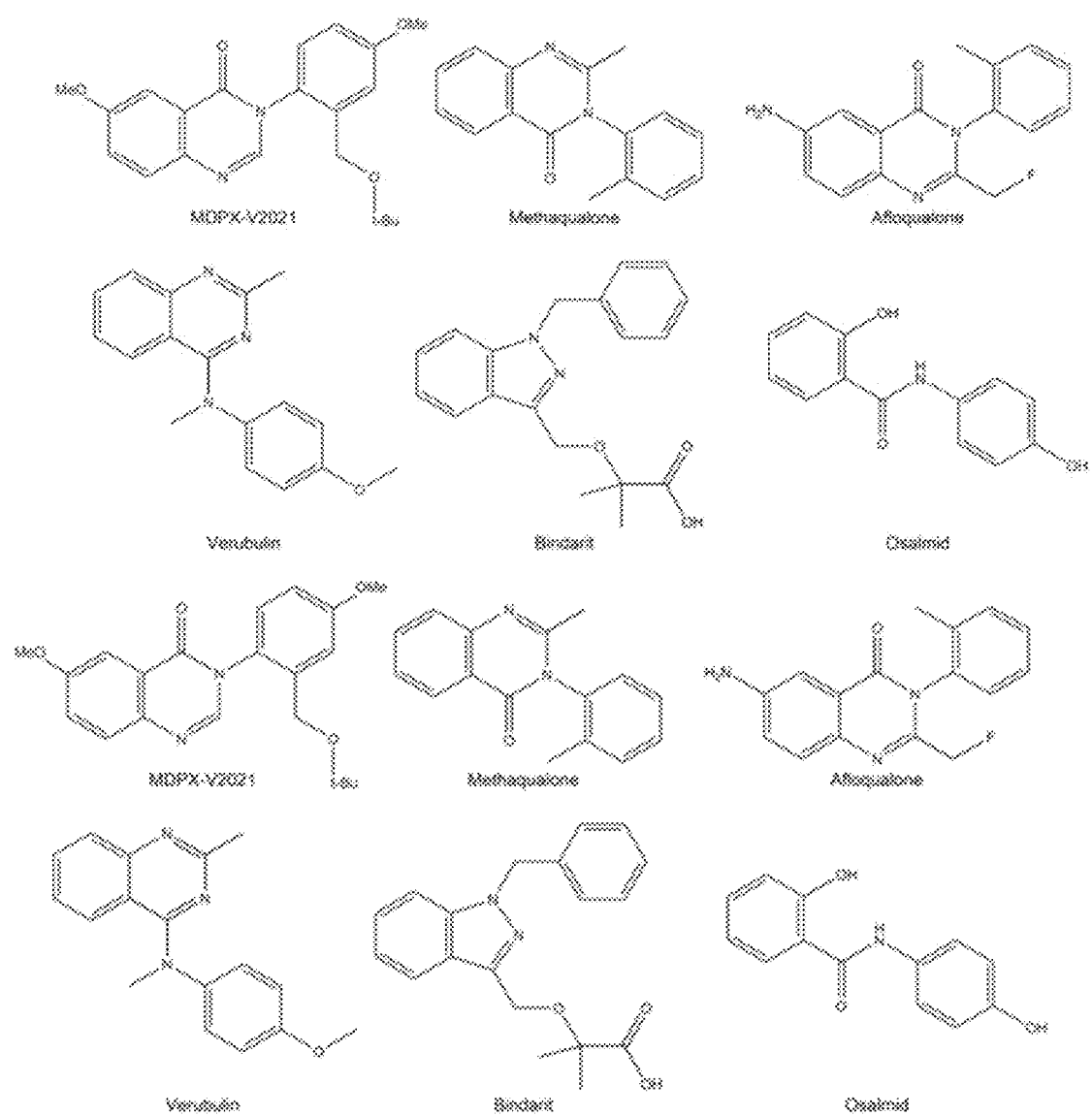

[FIG. 4]
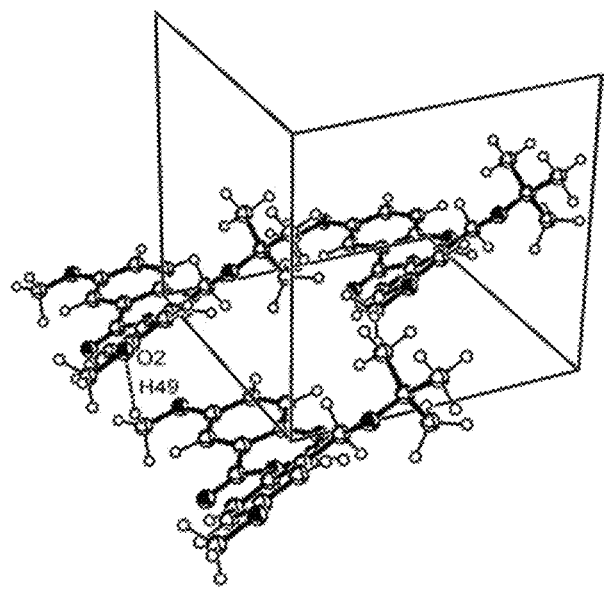
[FIG. 5]
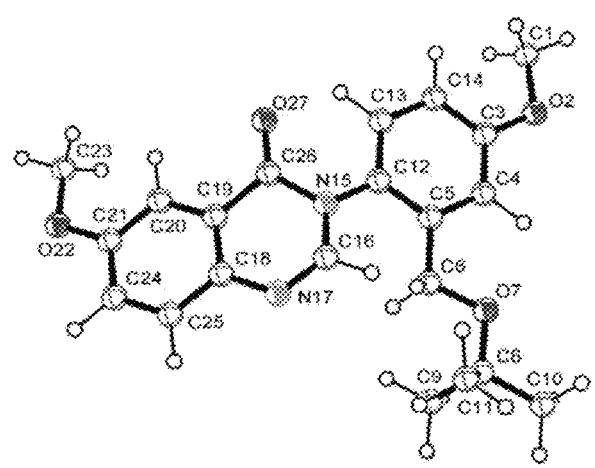

[FIG. 6]
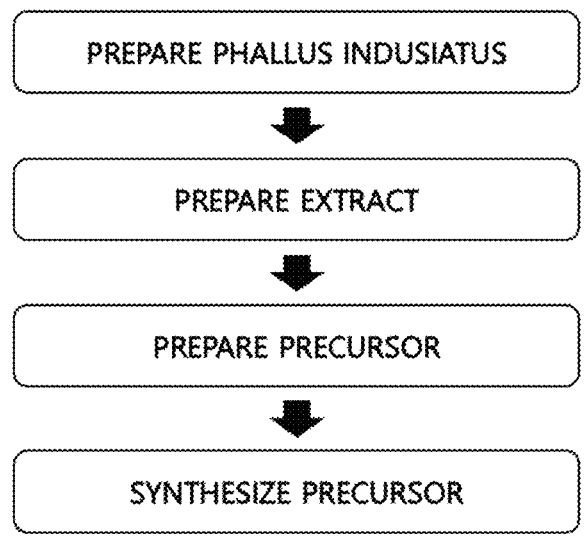

[FIG. 7]
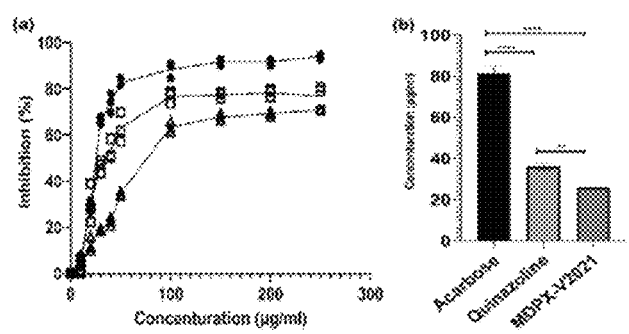
[FIG. 8]
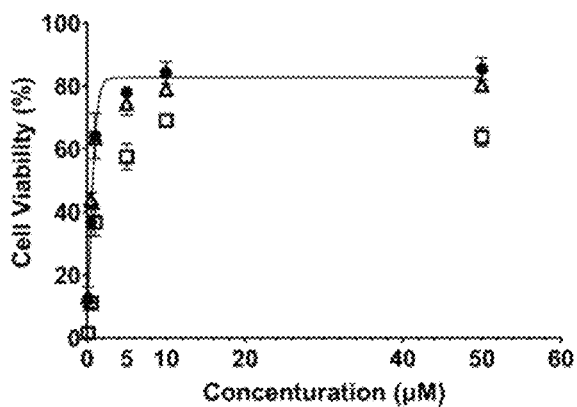

COMPOSITION FOR INHIBITING GROWTH OF SARS-COV-2 AND METHOD OF PREPARING THE SAME

CROSS-REFERENCE TO RELATED APPLICATION

This application claims priority to Korean Patent Application No. 10-2020-0134352, filed on Oct. 16, 2020 in the Korean Intellectual Property Office, the disclosure of which is incorporated herein by reference.

BACKGROUND OF THE DISCLOSURE

Field of the Disclosure

The present disclosure relates to a composition for inhibiting the growth of SARS-CoV-2, and more particularly to a composition for inhibiting the growth of SARS-CoV-2 including a component derived from *Phallus indusiatus*.

Description of the Related Art

SARS-CoV-2, which was first reported in Wuhan, China in December 2019, has spread globally, causing serious damage. As of Jul. 21, 2020, 14,538,115 cases have been confirmed in more than 188 countries, with 606,922 deaths. Currently, as there are efforts in each country to develop therapeutics and vaccines, several developments are being made for potential antiviral therapeutics. Efforts have been made in various countries to develop therapeutics and vaccines, and as a result, several potential antiviral therapeutics are currently being developed. Treatment can be divided into two categories depending on the goal. One is to regulate the human immune system by promoting an innate response to the virus or inhibiting the inflammatory process that causes lung damage. The other is to act directly on the virus by inhibiting the important viral enzyme responsible for gene replication or by blocking viral entry into human cells. The latter can be subdivided into blocking virus-cell membrane fusion (APN01, hydroxychloroquine, umifenovir); inhibiting the RNA-dependent RNA polymerase (remdesivir, favipiravir); and inhibiting viral protease (ivermectin, lopinavir/ritonavir). Most drugs under development were originally designed for other pathogens and quickly repurposed as treatments for COVID-19.

A brief summary of the SARS-CoV-2 replication cycle is as follows: (1) Viral entry is fused to the host membrane by binding of the angiotensin-converting enzyme (ACE 2) receptor and cleavage by the serine protease (TMPRSS2). (2) After uncoating and release of viral RNA into the cytoplasm, polyproteins, pp1a and pp1ab, are generated through translation of open reading frame 1a (ORF1a) and ORF1ab. These in turn are processed by viral proteases (encoded by ORF1a) to produce 16 non-structural proteins. The formation of the RNA replication-transcriptase complex (RTC) uses an endoplasmic reticulum (ER)-derived membrane. (3) Translated structural proteins and genomic RNA are assembled into viral nucleocapsids and envelopes in the ER-Golgi intermediate compartment and released by exocrine.

In the SARS-CoV-2 replication cycle, post-translational modification occurs during viral assembly and maturation. Post-translational modification (PTM) refers to the covalent modification of a protein after it is translated by the ribosome. By introducing new functional groups such as phosphate and carbohydrate, PTM expands the chemical repertoire of 20 standard amino acids while playing an important role in regulating folding, stability, enzymatic activity, intracellular location, and interactions between proteins. PTM involving structural changes in polypeptides includes proteolytic cleavage and disulfide bond formation, whereas PTM including addition of functional groups includes phosphorylation, glycosylation and lipidation (palmitoylation and myristoylation). In addition, proteins may be modified by covalent conjugation of one or more small proteins or peptides, as in the case of ubiquitination, SUMOylation, ISGylation, and NEDDylation.

Accordingly, the present disclosure sets a virus assembly part as a clear treatment target to solve the above problems, and proposes a substance capable of targeting glucosylation of the post-translational modification (PTM) stage that is the last stage of the SARS-CoV-2 replication cycle.

RELATED ART DOCUMENTS

Patent Documents

Korean Patent No. 10-0664724 "Manufacturing method of natural bactericide comprising extracts of *Dictyophora indusiata* and natural bactericide obtained therefrom"

Non-Patent Documents

Solomon Habtemariam, "The Chemistry, Pharmacology and Therapeutic Potential of the Edible Mushroom *Dictyophora indusiata* (Vent ex. Pers.) Fischer (Synn. *Phallus indusiatus*)". Biomedicines, 12 Dec. 2019.

SUMMARY OF THE DISCLOSURE

Therefore, the present disclosure has been made in view of the above problems, and it is an object of the present disclosure to provide MDPX-V2021 prepared using dictyoquinazol derived from *Phallus indusiatus*.

It is another object of the present disclosure to provide a composition for inhibiting the growth of virus which is capable of inhibiting the growth of SARS-CoV-2.

It is yet another object of the present disclosure to provide a method of preparing MDPX-V2021.

In accordance with an aspect of the present disclosure, the above and other objects can be accomplished by the provision of a composition for inhibiting the growth of virus, wherein the composition includes MDPX-V2021 represented by Formula 1 below, MDPX-V2021 serving to inhibit a post-translational modification (PTM) stage in cells after SARS-CoV-2 penetrates into the body:

[Formula 1]

3-{2-[(tert-butoxy)methyl]-4-methoxyphenyl}-6-methoxy-3,4-dihydroquinazolin-4-one MDPX-V2021 represented by Formula 1 may be synthesized from Dictyoquinazol A represented by Formula 2 below:

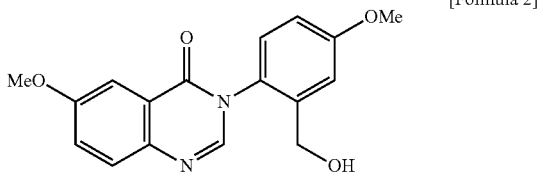
[Formula 2]

Dictyoquinazol A represented by Formula 2 may be derived from *Phallus indusiatus.*

MDPX-V2021 represented by Formula 1 may act as an antagonist against glycosylation in the PTM stage.
The antagonist may be an antagonist against α-glucosidase.

When MDPX-V2021 is synthesized, 4-dimethylaminopyridine and tert-butylalcohol may be used.

In accordance with another aspect of the present disclosure, there is provided a method of preparing a composition for inhibiting growth of virus, the method including: drying and preparing *Phallus indusiatus*; immersing the dried *Phallus indusiatus* in a solvent; decompressing the solvent, and then fractionating the solvent isolated through the decompressing to obtain a precursor; and synthesizing the obtained precursor to prepare MDPX-V2021 represented by Formula 1 below.

[Formula 1]

The solvent may be methanol or ethanol.

The precursor may be Dictyoquinazol A.

In the synthesizing, 4-dimethylaminopyridine and tert-butylalcohol may be used.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 illustrates a chemical formula of dictyoquinazol A;

FIG. 2 illustrates a structural formula and schematic diagram of a molecular structure of MDPX-V2021 according to an embodiment of the present disclosure;

FIG. 3 illustrates chemical structural formulas of MDPX-V2021 in a virus inhibition composition according to an embodiment of the present disclosure and drug components having structures similar to MDPX-V2021;

FIG. 4 illustrates a displacement ellipsoid drawn at a 50% probability level on the X-ray crystal structure of MDPX-V2021 in a virus inhibition composition according to an embodiment of the present disclosure;

FIG. 5 illustrates a schematic molecular packing diagram of MDPX-V2021 in a virus inhibition composition according to an embodiment of the present disclosure;

FIG. 6 illustrates a flowchart of a preparation method according to an embodiment of the present disclosure;

FIG. 7 illustrates alpha-glucosidase inhibition effects of virus inhibition compositions according to an example and comparative examples of the present disclosure; and FIG. 8 illustrates nerve cell protection ability of MDPX-V2021 in a virus inhibition composition according to an embodiment of the present disclosure.

DETAILED DESCRIPTION OF THE DISCLOSURE

The present disclosure will now be described more fully with reference to the accompanying drawings and contents disclosed in the drawings. However, the present disclosure should not be construed as limited to the exemplary embodiments described herein.

The terms used in the present specification are used to explain a specific exemplary embodiment and not to limit the present inventive concept. Thus, the expression of singularity in the present specification includes the expression of plurality unless clearly specified otherwise in context. It will be further understood that the terms "comprise" and/or "comprising", when used in this specification, specify the presence of stated components, steps, operations, and/or elements, but do not preclude the presence or addition of one or more other components, steps, operations, and/or elements thereof.

It should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

In addition, as used in the description of the disclosure and the appended claims, the singular forms "a", "an" and "the" are intended to include the plural forms as well, unless context clearly indicates otherwise.

In addition, when an element such as a layer, a film, a region, and a constituent is referred to as being "on" another element, the element can be directly on another element or an intervening element can be present.

Hereinafter, a composition for inhibiting the growth of virus according to an embodiment of the present disclosure is described in detail with reference to the accompanying drawings.

FIG. 1 illustrates the structure of dictyoquinazol A. Dictyoquinazol A is a material derived from *Phallus indusiatus*. In addition, *Phallus indusiatus* is a raw material of dictyoquinazol B and dictyoquinazol C in addition to dictyoquinazol A.

*Phallus indusiatus* is a mushroom belonging to Phallaceae of Phallales of Basidiomycota, and is mainly scattered or grows in groups on the ground in bamboo forests such as Korea, China, Taiwan, and Japan.

*Phallus indusiatus* is a decaying fungus that decomposes fallen leaves of bamboo to obtain nutrition therefrom. *Phallus indusiatus* mainly grows during the rainy season from July to August, when the temperature is high and precipitation is abundant.

In addition, *Phallus indusiatus* was classified as genus *Drittyyophora* by Nikase Auguste Desvaux in 1809, and was known as *Dittyophora indusiata* for a long time. Recent research focuses on the morphological similarity rather than the presence or absence of an indusium (a part that spreads like a skirt), and thus, *Dittyophora* is considered a synonym for *Phallus*.

Dictyoquinazol A forms 3-{2-[(tert-butoxy)methyl]-4-methoxyphenyl}-6-methoxy-3,4-dihydroquinazolin-4-one according to the synthesis (semi-synthesis) shown in Reaction Scheme 1 below.

[Reaction Scheme 1]

3-{2-[(tert-butoxy)methyl]-4-methoxyphenyl}-6-methoxy-3,4-dihydroquinazolin-4-one is hereinafter referred to as MDPX-V2021. MDPX-V2021 is the same as Formula 1, and three-dimensional structures thereof are illustrated in FIG. 2.

[Formula 1]

Referring to FIG. 2, (a) of FIG. 2 illustrates the chemical structural formula of MDPX-V2021, (b) of FIG. 2 illustrates the three-dimensional structural formula of MDPX-V2021, (c) of FIG. 2 illustrates Lowest Unoccupied Molecular Orbital (LUMO) calculated as having the lowest energy level among orbitals that are not filled with electrons, and (d) of FIG. 2 illustrates Highest Occupied Molecular Orbital (HOMO) calculated as having the highest energy level among orbitals occupied by electrons.

MDPX-V2021 Suppresses a Post-Translational Modification (PTM) Stage of SARS-CoV-2.

PTM of SARS-CoV-2 occurs in assembly and maturation stages thereof. Here, PTM refers to covalent modification of a protein after the protein is translated by the ribosome.

PTM expands the chemical repertoire of 20 standard amino acids by introducing new functional groups such as phosphate and carbohydrate, while playing an important role in regulating folding, stability, enzymatic activity, intracellular location, and the interaction between proteins.

PTM involving structural changes in polypeptides involves proteolytic cleavage and disulfide bond formation, whereas PTM with addition of functional groups include phosphorylation, glycosylation and lipidation. In addition, proteins may be modified by covalent conjugation of one or more small proteins or peptides, such as in the case of ubiquitination, SUMOylation, ISGylation, and NEDDylation.

MDPX-V2021 is Characterized by Inhibiting Glycosylation of PTM.

Glycosylation plays an important role in a wide range of biological processes, including cell adhesion to the extracellular matrix and intracellular protein-ligand interactions. There are a variety of glycosidic bonds including N-, O- and C-linked glycosylation, glypiation (GPI anchor attachment) and phosphoglycosylation. A common type is N-linked glycosylation. When glycans are translated and transported to the ER, they attach to an initial protein. 'N' in the name means that the glycan is uniformly bound to the carboxamido nitrogen of the asparagine (AsN or N) residue. N-linked glycosylation can be divided into (1) glycan assembly and attachment to a precursor, (2) glycan trimming, and (3) glycan maturation in the Golgi apparatus.

N-linked glycosylation is involved in neutralizing-epitope formation and lectin-mediated virion attachment in the spike (S) protein on the surface of a virus particle, and, in the envelope (E) protein, contributes to the topology of two membranes and affects the folding and trafficking of the membrane (M) protein.

N-linked glycosylation particularly contributes significantly to the morphology of the coronavirus S protein, and thus greatly affects the receptor binding and antigenicity of the S protein. There are a broad range of viral antigen-related responses. There is experimental evidence that the antigenicity of S and M proteins is significantly reduced when cells are infected with transmissible gastroenteritis coronavirus (TGEV) in the presence of tunicamycin that is an inhibitor of N-linked glycosylation. Further, the S protein of SARS-CoV binds to calnexin of the molecular chaperone during maturation in the ER. The SARS-CoV S-like virion produced from Calnexin-Knockdown cells contained S protein with abnormal N-glycans and had a significantly lower infection rate, compared to a control group. In mammals, N-linked glycans are removed and terminated sequentially by ER glucosidase I and II immediately after glycosylation at certain asparagine residues. In addition, the glucosidase reaction allows a glycoprotein to interact with ER chaperone calnexin and calreticulin. The interaction with calnexin promotes the correct folding of some glycoproteins. In summary, the use of glucosidase inhibitors induces misfolding of viral glycoproteins, preventing secretion of virion and preventing adhesion thereof.

In MDPX-V2021, quinazoline, which is the skeletal structure of dictyoquinazol, can act to inhibit alpha glucosidase. Accordingly, dictyoquinazol and derivatives thereof act as antagonists of alpha glucosidase (inhibitor), inhibiting the SARS-CoV-2 virus PTM process In addition, effects of releasing virus-derived neurotoxicity, encephalitis, hippocampal sclerosis, and stroke, which are the effects of existing dictyoquinazol, are exhibited.

Medicinal substances similar to MDPX-V2021 are shown in FIG. 3.

Referring to FIG. 3, Methaqualone, Afloqualone, Verubulin, Bindarit, and Osalmid are shown as medicinal substances similar to MDPX-V2021.

The crystal structure of MDPX-V2021 is schematically illustrated in FIG. 4.

As shown in the X-ray analysis of FIG. 4, there are six rotatable bonds, which indicated that the structure is flexible. In addition, there is no stereocenter. A distance between O2 and C24 is 10.3 Å (angstrom), and the distances and angles between main bonds are shown in Table 1 below.

The schematic molecular packing diagram of MDPX-V2021 is illustrated in FIG. 5. Referring to FIG. 5, it can be confirmed that the hydrogen bonding of MDPX-V2021 is typically formed in H49-O2 (bond length: 2.218 Å). This indicates that intermolecular disintegration of MDPX-V2021 can rapidly proceed because MDPX-V2021 is composed of a loose crystalline form.

TABLE 1

| Bond Length (Å) | | | |
|---|---|---|---|
| C(21)—C(24) | 1.393 | N(17)—C(18) | 1.405 |
| C(19)—C(26) | 1.502 | N(15)—C(26) | 1.447 |
| C(12)—N(15) | 1.345 | N(15)—C(16) | 1.364 |
| C(6)—O(7) | 1.402 | O(7)—C(8) | 1.402 |
| C(5)—C(12) | 1.395 | O(2)—C(3) | 1.355 |
| Bond Angle (°) | | | |
| C(19)—C(26)—N(15) | 111.480 | N(17)—C(16)—N(15) | 127.249 |
| C(18)—N(17)—C(16) | 116.464 | C(26)—N(15)—C(16) | 119.505 |
| C(26)—N(15)—C(12) | 120.246 | C(3)—O(2)—C(1) | 110.801 |
| Dihedral angle (°) | | | |
| C(18)—C(19)—C(26)—N(15) | 16.858 | C(20)—C(19)—C(26)—N(15) | −165.619 |
| N(17)—C(18)—C(19)—C(26) | −2.079 | C(12)—N(15)—C(26)—C(19) | 156.584 |
| C(6)—O(7)—C(8)—C(9) | 60.005 | C(5)—C(6)—O(7)—C(8) | 179.999 |

FIG. 6 illustrates a flowchart of a process of preparing a composition for inhibiting the growth of virus according to an embodiment of the present disclosure.

Referring to FIG. 6, the process of preparing a composition for inhibiting the growth of virus including a step of preparing *Phallus indusiatus*, a step of preparing an extract, a step of preparing a precursor and a step of synthesizing the precursor.

In the step of preparing *Phallus indusiatus*, fruit bodies of *Phallus indusiatus* may be dried at 50° C. to 70° C. for 18 hours to 30 hours. Particularly, the fruit bodies are hot-air-dried at 60° C. for 24 hours.

In the step of preparing an extract, the dried *Phallus indusiatus* fruit bodies are immersed in a lower alcohol solvent for one day to prepare an extract.

The lower alcohol solvent may be methanol or ethanol.

The step of synthesizing the precursor further includes a step of decompressing the prepared extract to separate the solvent therefrom and a step of fractionating the solvent to produce a precursor.

The fractionation may be performed using a column. The column may be charged with a large exclusion column such as Sephadex LH-20, a reversed phase column such as YMC ODC-H80, or an ion exchange column such as Diaion HP-20.

The step of synthesizing the precursor may include a step of adding ethyl acetate, 4-dimethylaminopyridine, and tert-butyl alcohol to the precursor and stirring the same, and, as subsequent steps, may further include a step of adding copper sulfate (Copper (ii) sulfate) and allowing reaction to proceed, and a step of performing concentration to obtain crystals.

Example 1

1.12 kg of *Phallus indusiatus* was purchased from Baekasan Food (48 Icheon-ri, Buk-myeon, Hwasun-gun, Jeollanam-do). Fruit bodies of *Phallus indusiatus* and egg samples were dried in a 60° C. hot air dryer for 24 hours. 310 g of the dried sample was extracted twice with methanol for 1 day at room temperature. After removing the methanol under reduced pressure, a resultant solution was injected into a Diaion HP-20 column. The column was washed with purified water and eluted with 30% aqueous methanol. The eluent was concentrated in a vacuum to evaporate methanol, and then the concentrate was partitioned between ethyl acetate and water. A soluble portion of ethyl acetate was eluted with 70% aqueous methanol and separated on a Sephadex LH-20 column, and then a total of 21.30 mg of precursor was obtained through preparative HPLC using a YMC ODS-H80 column, and 60% aqueous methanol as a mobile phase.

Next, a dry-treated 50 mL 3-neck round bottom flask equipped with an egg-shaped stir bar was cooled to 30° C., and the obtained precursor (21.30 mg, 0.068 mmol) was fed thereinto, followed by sequential addition of ethyl acetate (5 mL), 4-dimethylaminopyridine (1.5 mg, 0.012 mmol) and tert-butyl alcohol (10 mL). After stirring the heterogeneous slurry at 65° C. for 12 hours, a pale yellow reaction mixture was obtained. Next, copper (ii) sulfate (1% aq; 30 mL) was added to dilute the reaction mixture, and then allowed to stand at room temperature for 6 hours.

Next, the resultant mixture was concentrated in a vacuum using a rotary evaporator (25° C., 7.5 mmHg) to obtain an organic layer. The obtained organic layer was directly transferred to a Buchner funnel and vacuum-filtered to obtain crystals. The obtained crystals were dried in the presence of $MgSO_4$. As a results, >19.81 mg of MDPX-V2021, as a pale yellow crystal product having a purity greater than 96% (93% yield), was obtained.

Comparative Example 1

Commercial materials, Methaqualone, Afloqualone, Verubulin, Bindarit, and Osalmid, exhibiting similar effects to those of MDPX-V2021 prepared according to the example of the present disclosure were prepared.

Comparative Example 2

Quinazoline and Acrbose purchased from Sigma-Aldrich (US) were prepared to compare the structural relationship with MDPX-V2021 prepared according to the example of the present disclosure.

Comparative Example 3

To compare nerve cell protection ability, MK-801 purchased from Sigma-Aldrich (US) and MDPX-V2021 prepared according to the example of the present disclosure were prepared.

Property Evaluation 1

The distribution coefficient, molecular flexibility and shape index of each of the samples prepared according to Example 1 and Comparative Example 1 were investigated.

Results are summarized in Table 2 below.

TABLE 2

| Sample name | MDPX-V2021 | Methaqualone | Afloqualone | Verubulin | Bindarit | Osalmid |
|---|---|---|---|---|---|---|
| Molweight | 368.43 | 250.30 | 283.31 | 279.34 | 324.38 | 229.23 |
| Calculation Distribution Coefficient (cLogP) | 3.15 | 2.88 | 1.98 | 2.48 | 2.15 | 2.12 |
| H-Acceptors | 6 | 3 | 4 | 4 | 5 | 4 |
| H-Donors | 0 | 0 | 1 | 0 | 1 | 3 |
| Non-H Atoms | 27 | 19 | 21 | 21 | 24 | 17 |
| Non-C—H Atoms | 6 | 3 | 5 | 4 | 5 | 4 |
| Electronegative Atoms | 6 | 3 | 5 | 4 | 5 | 4 |
| Stereo Centers | 0 | 0 | 0 | 0 | 0 | 0 |
| Rotatable Bonds | 6 | 1 | 2 | 3 | 6 | 2 |
| Aromatic Atoms | 12 | 12 | 12 | 16 | 15 | 12 |
| sp3-Atoms | 10 | 2 | 2 | 4 | 7 | 2 |
| Symmetric atoms | 2 | 0 | 0 | 2 | 3 | 2 |
| Amides | 1 | 1 | 1 | 0 | 0 | 1 |
| Amines | 0 | 0 | 1 | 0 | 0 | 0 |
| Aromatic Amines | 0 | 0 | 1 | 0 | 0 | 0 |
| Acidic Oxygens | 0 | 0 | 0 | 0 | 1 | 0 |
| PSA | 60.36 | 32.67 | 58.69 | 38.25 | 64.35 | 69.56 |
| Shape Index | 0.48 | 0.53 | 0.48 | 0.57 | 0.54 | 0.65 |
| Molecular Flexibility | 0.45 | 0.28 | 0.29 | 0.34 | 0.48 | 0.47 |
| Molecular Complexity | 0.86 | 0.82 | 0.86 | 0.82 | 0.80 | 0.62 |

Referring to Table 2, it can be confirmed that, when compared to drugs having structures similar to that of MDPX-V2021, MDPX-V2021 has a relatively high calculation distribution coefficient, molecular flexibility, and shape index, thus having a high absorption rate. In particular, since the major condition of SARS-CoV-2 causes fatal damage to the lungs, direct local deposition and administration to the lungs can be expected to be effective, and a route for systemic delivery is also possible.

Property Evaluation 2

The properties of MDPX-V2021 prepared according to Example 1 are evaluated.

Evaluation results are summarized in Table 3 below.

TABLE 3

| Property Name | Property Value |
|---|---|
| Boiling point | 498.13° C. |
| Melting point | 211.73° C. |
| Vapor Pressure (T = 298.15K) | 4.23E−08Pa |
| Critical Temperature | 694.02° C. |
| Critical Pressure | 16.92 bar |
| Critical Volume | 1056.50 cm$^3$/mol |
| Gibbs Energy (T = 298.15K, p = 1atm) | 163.74 kJ/mol |
| Heat of Formation (T = 298.15K, p = 1atm) | −341.46 kJ/mol |
| Log Distribution Coefficient (LogP) | 3.17 |
| Octanol-air Distribution Coefficient (Log Koa) | 15.02 |
| Water Solubility (T = 298.15K) | 2.11 mg/L |
| Molar Refractivity | 103.26 cm$^3$/mol |

First, drug deposition due to aerosol administration in in the lungs and respiratory tracts is mainly caused by three mechanisms: gravity sedimentation, inertial collision and diffusion. In addition, the size and geometry of particles or droplets, in addition to the morphological aspects of the lungs and ventilation parameters, should also be analyzed to determine the absorption strength of suitable drugs. In other words, surface charges, particle or droplet sizes, and the shape and hygroscopicity of particulates also affect drug deposition through the lung pathway. Referring to Table 3, MDPX-V2021 has a crystal structure in a solid state at room temperature, and the partition coefficient (Log P) and Octanol-air distribution coefficient (Log Koa), which are indicators of the drug's lipophilicity, are 3.17 and 15.02, respectively, which indicates that MDPX-V2021 is advantageous for drug deposition through the lung pathway. In particular, the Octanol-air distribution coefficient of Abamis (ingredient name: fluticasone) as an allergic rhinitis treatment manufactured by GSK is calculated as 8.429, whereas the Octanol-air distribution coefficient of MDPX-V2021 is 15.02. Accordingly, MDPX-V2021 is well adsorbed by the alveoli without being mixed and escaping with air after being introduced into the alveoli, compared to Abamis.

Property Evaluation 3

Using the samples prepared according to Example 1 and Comparative Examples 2 and 3, inhibitory activity against α-glucosidase was evaluated to analyze activity based on structural analogs.

50 μl of phosphate buffer (100 mM, pH=6.8), 10 μl of α-glucosidase (1 U/ml) and 20 μl of each of samples at various concentrations (0.01, 0.02, 0.03, 0.04, 0.05, 0.1, 0.15, 0.2 and 0.25 mg/ml) of Example 1 and Comparative Example 2 were fed into 96-well plates and pre-incubated at 37° C. for 15 minutes. Next, 20 μl of P-NPG (5 mM) was added as a substrate and further incubated at 37° C. for 20 minutes. This reaction was stopped by adding 50 μl of Na2CO$_3$ (0.1 M). The absorbance of released p-nitrophenol was measured at 405 nm using a multi-mode plate reader. Acarbose was set as a positive control. Each experiment was performed three times. An inhibition rate (%) was evaluated using the following equation (inhibition (%)=[1−(sample/control)]×100). IC$_{50}$ values were calculated by regression analysis, and the results are shown in FIG. 7 and Table 4.

Referring to FIG. 7, Acarbose was indicated as A, Quinazoline was indicated as □, and MDPX-V2021 was indicated as ● on the graph. It can be confirmed that MDPX-V2021 has inhibitory activity against α-glucosidase at concentrations of 0.01, 0.02, 0.03, 0.04, 0.05, 0.1, 0.15, 0.2 and 0.25 mg/ml. When comparing the antagonism of drugs through IC$_{50}$, MDPX-V2021 shows remarkable efficacy compared to Acarbose, and shows stable antagonism compared to Quinazoline having structural similarity (MCS Tanimoto: 0.3704).

TABLE 4

| Sample Name | Structure | α-glucosidase inhibition IC$_{50}$ (μg/mL) | Cell viability from excitotoxin-induced neuron toxicity (%) |
| --- | --- | --- | --- |
| Quinazol A | [6-methoxy-3-(4-methoxy-2-(hydroxymethyl)phenyl)quinazolin-4(3H)-one] | NT | 68.910 ± 1.406 |
| MDPX-V2021 | [6-methoxy-3-(4-methoxy-2-((tert-butoxymethyl))phenyl)quinazolin-4(3H)-one] | 25.962 ± 0.357 | 84.083 ± 3.482 |
| Quinazoline | [quinazoline] | 36.162 ± 1.789 | NT |
| Acarbose | [acarbose structure] | 81.528 ± 3.651 | NT |
| MK-801 | [MK-801 structure] | NT | 78.830 ± 0.567 |

Property Evaluation 4

Nerve cell protection ability was evaluated using Quinazole and MDPX-V2021 prepared according to Example 1 and MK-801 prepared according to Comparative Example 3.

To evaluate the neuroprotective activity of Quinazole, MDPX-V2021 and MK-801 against damage due to excitotoxin, each of the samples was dissolved in ethanol (final concentration, 0.1%), and a 12-day-old cortical cell cultures were used. The cultures were respectively pre-treated with the samples for 1 hour and then exposed to 20 μM glutamate, 80 μM α-amino-3-hydroxy-5-methyl-4-isoxazolepropionic acid, 40 μM N-Methyl-D-aspartic acid and 200 μM kinate. Next, each of the cultures was additionally cultured in neurobasal medium for one day, and the survival rate of the nerve cells was measured by MTT assay.

MTT tetrazolium (1 mg/mL) was added to neurons grown in 96-well plate, and then cultured at 37° C. for 1 hour. The reaction medium was carefully sucked, and then DMSO was added thereto to dissolve the blue formazan product. The survival rate of the nerve cells was estimated by quantifying an available formazan at 540 nm using a multi-mode plate reader. The test was repeated 3 times, and the cell viability was calculated according to 100×(excitotoxin OD+sample treatment-excitotoxin treatment OD)/(control OD-excitotoxin treatment OD).

Results are shown in FIG. 8 and Table 4.

Referring to FIG. 8 and Table 4, the cell viability was significantly higher in MDPX-V2021, than in Quinazole, in a sample concentration range of 0.1 to 50 μM. In addition, from the sample concentration of 10 μM, MDPX-V2021 was slightly higher than MK-801 and showed a stable survival rate. In addition, from the sample concentration of 10 μM, the cell viability of MDPX-V2021 was slightly higher than that of MK-801 and was stable.

Based on Property Evaluations 1 to 5, it can be confirmed that inhibition of MDPX-V2021 against α-glucosidase inhibits the PTM process corresponding to the final replication cycle of SARS-CoV-2. This indicates that MDPX-V2021 is a glucosidase inhibitor. Accordingly, MDPX-V2021 will inhibit the growth of SARS-CoV-2. In addition, MDPX-V2021 was experimentally proven to have a neuroprotective effect even in neurological inflammation caused by viral infection.

In addition, molecular packing of MDPX-V2021 is inferred to allow rapid absorption into lungs, etc., through a nebulizer. Further, it was confirmed that MDPX-V2021 can be easily prepared into co-crystals in the future. A side reactant in the synthesis process of MDPX-V2021 is $H_2O$. Accordingly, the present disclosure aims for green chemistry.

As apparent from the above description, provided is Formula 1 named as MDPX-V2021 according to an embodiment of the present disclosure.

In addition, a composition for inhibiting the growth of virus including MDPX-V2021 according to the embodiment is provided.

In addition, the composition for inhibiting the growth of virus according to the embodiment has an effect of inhibiting the post-translational modification (PTM) stage after translation of SARS-CoV-2.

Further, the composition for inhibiting the growth of virus according to the embodiment has an effect of inhibiting the PTM stage after translation of SARS-CoV-2 to inhibit the growth of SARS-CoV-2.

Although the present disclosure has been described through limited examples and figures, the present disclosure is not intended to be limited to the examples. Those skilled in the art will appreciate that various modifications, additions and substitutions are possible, without departing from the scope and spirit of the disclosure. Therefore, it should be understood that there is no intent to limit the disclosure to the embodiments disclosed, rather, the disclosure is to cover all modifications, equivalents, and alternatives falling within the spirit and scope of the disclosure as defined by the claims.

What is claimed is:

1. A composition for inhibiting the growth of virus, wherein the composition comprises MDPX-V2021 represented by Formula 1 below, MDPX-V2021 serving to inhibit a post-translational modification (PTM) stage in cells after SARS-CoV-2 penetrates into the body:

[Formula 1]

2. The composition according to claim 1, wherein MDPX-V2021 represented by Formula 1 is synthesized from Dictyoquinazol A represented by Formula 2 below:

[Formula 2]

3. The composition according to claim 2, wherein Dictyoquinazol A represented by Formula 2 is derived from *Phallus indusiatus*.

4. The composition according to claim 1, wherein MDPX-V2021 represented by Formula 1 acts as an antagonist against glucosylation in the PTM stage.

5. The composition according to claim 4, wherein the antagonist is an antagonist against α-glucosidase.

6. The composition according to claim 2, wherein, when MDPX-V2021 is synthesized, 4-dimethylaminopyridine and tert-butylalcohol are used.

7. A method of preparing a composition for inhibiting growth of virus, the method comprising:

drying and preparing *Phallus indusiatus*;

immersing the dried *Phallus indusiatus* in a solvent to prepare an extract;

decompressing the extract, and then fractionating the solvent isolated through the decompressing to obtain a precursor; and synthesizing the obtained precursor to prepare MDPX-V2021 represented by Formula 1 below:

[Formula 1]
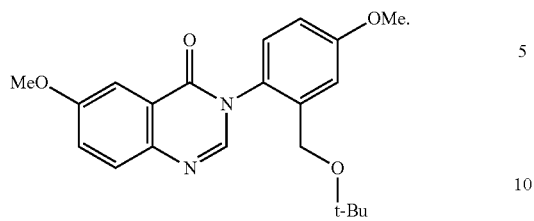
8. The method according to claim 7, wherein the solvent is methanol or ethanol.
9. The method according to claim 7, wherein the precursor is Dictyoquinazol A.
10. The method according to claim 7, wherein, in the synthesizing, 4-dimethylaminopyridine and tert-butylalcohol are used.
* * * * *